United States Patent
Gewehr et al.

(10) Patent No.: US 8,871,679 B2
(45) Date of Patent: Oct. 28, 2014

(54) FUNGICIDAL MIXTURES COMPRISING SUBSTITUTED 1-METHYLPYRAZOL-4-YLCARBOXANILIDES

(75) Inventors: Markus Gewehr, Kastellaun (DE); Ulf Groeger, Neuhofen (DE); Egon Haden, Ludwigshafen (DE); Michael Vonend, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 585 days.

(21) Appl. No.: 13/002,127

(22) PCT Filed: Jul. 2, 2009

(86) PCT No.: PCT/EP2009/058298
§ 371 (c)(1),
(2), (4) Date: Dec. 30, 2010

(87) PCT Pub. No.: WO2010/000790
PCT Pub. Date: Jan. 7, 2010

(65) Prior Publication Data
US 2011/0098176 A1    Apr. 28, 2011

(30) Foreign Application Priority Data
Jul. 4, 2008   (EP) .................................... 08159723

(51) Int. Cl.
| | |
|---|---|
| *A01N 43/08* | (2006.01) |
| *A01N 43/36* | (2006.01) |
| *A01N 43/38* | (2006.01) |
| *A01N 53/00* | (2006.01) |
| *A01N 53/02* | (2006.01) |
| *A01N 53/08* | (2006.01) |
| *A01N 53/14* | (2006.01) |
| *A01P 3/00* | (2006.01) |
| *A01N 43/56* | (2006.01) |

(52) U.S. Cl.
CPC ...................... *A01N 43/56* (2013.01)
USPC ........... 504/100; 514/406; 514/421; 514/461; 514/521; 514/531

(58) Field of Classification Search
USPC ........... 504/100; 514/521, 531, 406, 421, 461
See application file for complete search history.

(56) References Cited

U.S. PATENT DOCUMENTS

| | | |
|---|---|---|
| 3,991,071 A | 11/1976 | Brookes et al. |
| 5,013,659 A | 5/1991 | Bedbrook et al. |
| 5,330,995 A | 7/1994 | Eicken et al. |
| 5,438,070 A | 8/1995 | Eicken et al. |
| 5,476,868 A | 12/1995 | Wingert et al. |
| 5,877,194 A | 3/1999 | Colliot et al. |
| 5,972,971 A | 10/1999 | Heuer et al. |
| 6,147,104 A | 11/2000 | Eicken et al. |
| 7,329,633 B2 | 2/2008 | Dunkel et al. |
| 7,538,073 B2 | 5/2009 | Elbe et al. |
| 2002/0137759 A1 | 9/2002 | Schneidersmann et al. |
| 2003/0130119 A1 | 7/2003 | Watrin |
| 2005/0119229 A1 | 6/2005 | Ammermann et al. |
| 2005/0124815 A1 | 6/2005 | Elbe et al. |
| 2006/0116414 A1 | 6/2006 | Dunkel et al. |
| 2007/0060579 A1 | 3/2007 | Wachendorff-Neumann et al. |
| 2007/0093543 A1 | 4/2007 | Begliomini et al. |
| 2008/0039481 A1 | 2/2008 | Kemper et al. |
| 2008/0153707 A1* | 6/2008 | Gewehr et al. ................. 504/282 |
| 2008/0153824 A1 | 6/2008 | Speakman et al. |
| 2008/0293566 A1 | 11/2008 | Suty-Heinze et al. |
| 2008/0306119 A1 | 12/2008 | Steiner et al. |

(Continued)

FOREIGN PATENT DOCUMENTS

| | | |
|---|---|---|
| AU | 735903 | 10/1999 |
| CA | 2 543 053 | 5/2005 |

(Continued)

OTHER PUBLICATIONS

HCAPLUS abstract 2006:816176; abstracting JP 2006-213665 (2006).*

(Continued)

*Primary Examiner* — John Pak
(74) *Attorney, Agent, or Firm* — Brinks Gilson & Lione

(57) ABSTRACT

Fungicidal mixtures, comprising as active components 1) at least one 1-methylpyrazol-4-ylcarboxanilide of the formula I where $R^1=C_1$-$C_4$-alkyl or $C_1$-$C_4$-haloalkyl, $R^2$=hydrogen or halogen, X=hydrogen or halogen, Q=direct bond, a cyclopropylene or an anellated bicyclo[2.2.1]heptane ring; $R^3=C_1$-$C_6$-alkyl, cyclopropyl or phenyl substituted with two or three halogen atoms or a trifluoromethylthio radical; and 2) at least one active compound II, selected from the active compound groups A) to K): A) organo(thio)phosphates; B) carbamates; C) pyrethroids; D) growth regulators; E) GABA antagonist compounds; F) macrocyclic lactone insecticides; G) METI I acaricides; H) METI II and III compounds; J) oxidative phosphorylation inhibitor compounds; K) various compounds; in a synergistically effective amount, methods for controlling harmful fungi using mixtures of at least one compound I and at least one active compound II, the use of a compound I or compounds I with active compounds II for preparing such mixtures, and also compositions and seed comprising such mixtures.

(I)

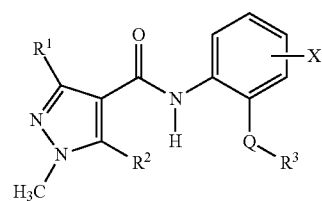

17 Claims, No Drawings

(56) References Cited

U.S. PATENT DOCUMENTS

| | | |
|---|---|---|
| 2009/0018015 A1 | 1/2009 | Wachendorff-Neumann et al. |
| 2009/0320166 A1 | 12/2009 | Suty-Heinze et al. |
| 2010/0062938 A1 | 3/2010 | Voeste et al. |
| 2011/0105576 A1 | 5/2011 | Zeun et al. |

FOREIGN PATENT DOCUMENTS

| | | |
|---|---|---|
| CA | 2 580 371 | 9/2005 |
| CA | 2 611 178 | 12/2006 |
| DE | 195 48 873 | 7/1997 |
| EP | 0 142 924 | 5/1985 |
| EP | 0 193 259 | 9/1986 |
| EP | 0 242 236 | 10/1987 |
| EP | 0 242 246 | 10/1987 |
| EP | 0 257 993 | 3/1988 |
| EP | 0 267 778 | 5/1988 |
| EP | 545099 | 6/1993 |
| EP | 589301 | 3/1994 |
| EP | 0 645 091 | 3/1995 |
| EP | 0 951 831 | 10/1999 |
| JP | 2006-213665 * | 8/2006 |
| WO | WO 91/13972 | 9/1991 |
| WO | WO 91/19806 | 12/1991 |
| WO | WO 92/00377 | 1/1992 |
| WO | WO 92/11376 | 7/1992 |
| WO | WO 92/14827 | 9/1992 |
| WO | WO 95/00303 | 1/1995 |
| WO | WO 95/12314 | 5/1995 |
| WO | WO 99/09013 | 2/1999 |
| WO | WO 99/48366 | 9/1999 |
| WO | WO 00/28825 | 5/2000 |
| WO | WO 02/102148 | 12/2002 |
| WO | WO 03/010149 | 2/2003 |
| WO | WO 03/070705 | 8/2003 |
| WO | WO 03/074491 | 9/2003 |
| WO | WO 03/075653 | 9/2003 |
| WO | WO 2004/035589 | 4/2004 |
| WO | WO 2005/034628 | 4/2005 |
| WO | WO 2005/041653 | 5/2005 |
| WO | WO 2005/044002 | 5/2005 |
| WO | WO 2005/051081 | 6/2005 |
| WO | WO 2005/058040 | 6/2005 |
| WO | WO 2005/122772 | 12/2005 |
| WO | WO 2006/015865 | 2/2006 |
| WO | WO 2006/015866 | 2/2006 |
| WO | WO 2006/037632 | 4/2006 |
| WO | WO 2006/037634 | 4/2006 |
| WO | WO 2006/066810 | 6/2006 |
| WO | WO 2006/087343 * | 8/2006 |
| WO | WO 2006/114212 | 11/2006 |
| WO | WO 2006/131230 | 12/2006 |
| WO | WO 2007/017256 | 2/2007 |
| WO | WO 2007/068417 | 6/2007 |
| WO | WO 2007/090623 | 8/2007 |
| WO | WO 2007/115765 | 10/2007 |
| WO | WO 2007/128756 | 11/2007 |
| WO | WO 2007/131678 | 11/2007 |
| WO | WO 2008/003403 | 1/2008 |
| WO | WO 2008/095913 | 8/2008 |
| WO | WO 2008/113654 | 9/2008 |
| WO | WO 2008/132021 | 11/2008 |
| WO | WO 2009/056620 | 5/2009 |
| WO | WO 2009/106633 | 9/2009 |
| WO | WO 2009135834 | 11/2009 |
| WO | WO 2010/000790 | 1/2010 |

OTHER PUBLICATIONS

Machine translation of JP 2006-213665 (2006).*
HCAPLUS Abstract 1993:2281183 (1993).
HCAPLUS Abstract 1980: 599090 (1980).
Anonymous, "Method for protecting useful plants or plant propagation material", Kenneth Mason Publication, Research Disclosure, 207(7), 2006, 783 RD 507002.
Office Action dated Mar. 21, 2012, in U.S. Appl. No. 12/525,321.
Office Action dated Nov. 1, 2012, in U.S. Appl. No. 12/525,321.
International Search Report issued in PCT/EP2009/058298, filed Jul. 2, 2009.
International Preliminary Report on Patentability, issued in PCT/EP2009/058298, filed Jul. 2, 2009.
Office Action dated Jan. 16, 2013, in U.S. Appl. No. 12/991,295.
Office Action dated Jul. 17, 2013, in U.S. Appl. No. 12/991,295.

* cited by examiner

FUNGICIDAL MIXTURES COMPRISING SUBSTITUTED 1-METHYLPYRAZOL-4-YLCARBOXANILIDES

This application is a National Stage application of International Application No. PCT/EP2009/058298, filed Jul. 2, 2009, the entire contents of which is hereby incorporated herein by reference. This application also claims priority under 35 U.S.C. §119 to European Patent Application No. 08159723.9, filed Jul. 4, 2008, the entire contents of which is hereby incorporated herein by reference.

The present invention relates to mixtures for controlling phytopathogenic harmful fungi comprising, as active components, 1) at least one 1-methylpyrazol-4-ylcarboxanilides of the formula I

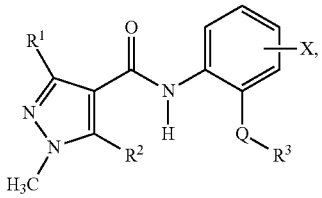

in which the substituents are as defined below:
$R^1$ is $C_1$-$C_4$-alkyl or $C_1$-$C_4$-haloalkyl;
$R^2$ is hydrogen or halogen;
X is hydrogen or fluorine;
Q is a direct bond, a cyclopropylene or an anellated bicyclo [2.2.1]heptane ring;
$R^3$ is $C_1$-$C_6$-alkyl, cyclopropyl or phenyl substituted with two or three halogen atoms or with a trifluoromethylthio radical;
and
2) at least one active compound II, selected from the active compound groups A) to K):
  A) organo(thio)phosphates selected from the group consisting of acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxy-demeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos and trichlorfon;
  B) carbamates selected from the group consisting of: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb and tri-azamate;
  C) pyrethroids selected from the group consisting of allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin and dimefluthrin;
  D) growth regulators selected from the group consisting of the following
    a) chitin synthesis inhibitors: benzoylureas: chlorfluazuron, cyramazin, -flucycloxuron, hexaflumuron, lufenuron, novaluron, triflumuron; buprofezin, diofenolan, hexythiazox, etoxazole and clofentazine;
    b) ecdysone antagonists: halofenozide, methoxyfenozide, tebufenozide, and azadirachtin;
    c) juvenoids: pyriproxyfen, methoprene and fenoxycarb;
    d) lipid biosynthesis inhibitors: spirodiclofen, spiromesifen and spirotetramat;
  E) GABA antagonist compounds selected from the group consisting of endosulfan, ethiprole, vaniliprole, pyrafluprole, pyriprole and the phenylpyrazole of the formula $E^1$

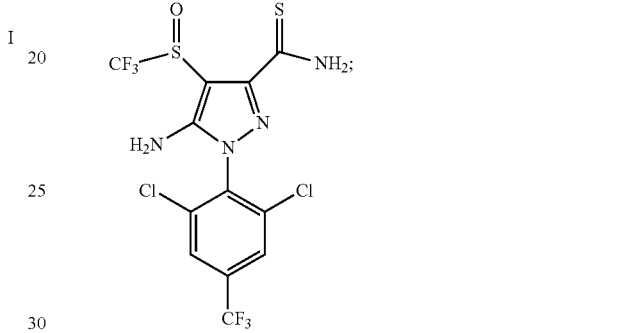

F) macrocyclic lactone insecticides selected from the group consisting of abamectin, emamectin, milbemectin, lepimectin, spinosad and spinetoram;
  G) METI I acaricides selected from the group consisting of fenazaquin, pyridaben, tebufenpyrad, tolfenpyrad and flufenerim;
  H) METI II and III compounds selected from the group consisting of acequinocyl, fluacyprim and hydramethylnon;
  J) oxidative phosphorylation inhibitor compounds selected from the group consisting of cyhexatin, diafenthiuron, fenbutatin oxide and propargite;
  K) various compounds selected from the group consisting of amidoflumet, benclothiaz, bifenazate, bistrifluron, cartap, chlorfenapyr, cryomazine, cyazypyr (HGW86), cyenopyrafen, cyflumetofen, flonicamid, flubendiamide, flupyrazofos, imicyafos, indoxacarb, metaflumizone, piperonyl butoxide, pymetrozine, pyridalyl, pyrifluquinazon, thiocyclam and the thiazole compound of formula $K^1$

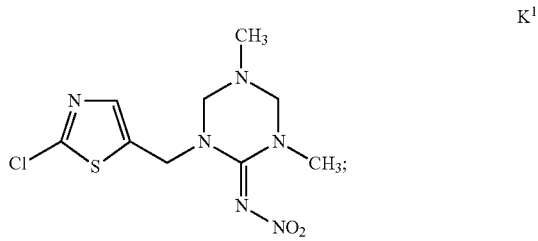 [SMILES: CN1CN(C)/C(=N\[N+](=O)[O-])N(Cc2cnc(Cl)s2)C1]

in a synergistically effective amount.

Moreover, the invention relates to a method for controlling harmful fungi using a mixture of at least one compound I and at least one of the active compounds II, to the use of the compound(s) I with active compound(s) II for preparing such mixtures, and also to compositions and seed comprising such mixtures.

The 1-methylpyrazol-4-ylcarboxanilides of the formula I, referred to above as component 1), their preparation and their action against harmful fungi are known from the literature (cf., for example, EP-A 545 099, EP-A 589 301, WO 99/09013, WO 03/010149, WO 2003/70705, WO 03/074491 and WO 04/035589), or they can be prepared in the manner described therein.

However, the known 1-methylpyrazol-4-ylcarboxanilides of the formula I are, in particular at low application rates and with regard to their spectrum of activity, not entirely satisfactory.

The active compounds II mentioned above as component 2), their preparation and their action against harmful fungi are generally known (cf., for example, http://www.hclrss.demon.co.uk/index.html); they are commercially available.

It is an object of the present invention, with a view to reducing the application rates and broadening the activity spectrum of the compounds I, to provide mixtures which, at a reduced total amount of active compounds applied, have improved activity against harmful fungi, in particular for specific indications.

We have accordingly found that this object is achieved by the mixtures, defined at the outset, of the active compounds I and II. Moreover, we have found that simultaneous, that is joint or separate, application of at least one compound I and at least one of the active compounds II or successive application of the compound(s) I and at least one of the active compounds II allows better control of harmful fungi than is possible with the individual compounds alone (synergistic mixtures).

By simultaneous, that is joint or separate, application of compound(s) I with at least one active compound II, the fungicidal activity is increased in a superadditive manner.

The compounds I can be present in different crystal modifications, which may differ in biological activity.

In the formula I, halogen is fluorine, chlorine, bromine or iodine, preferably fluorine or chlorine;

$C_1$-$C_4$-alkyl is methyl, ethyl, n-propyl, 1-methylethyl, n-butyl, 1-methylpropyl, 2-methylpropyl or 1,1-dimethylethyl, preferably methyl or ethyl;

$C_1$-$C_4$-alkyl is methyl, ethyl, n-propyl, 1-methylethyl, n-butyl, 1-methylpropyl, 2-methylpropyl, 1,1-dimethylethyl, n-pentyl, n-hexyl or 1,3-dimethylbutyl, in particular 1-methylethyl or 1,3-dimethylbutyl;

$C_1$-$C_4$-haloalkyl is a partially or fully halogenated $C_1$-$C_4$-alkyl radical, where the halogen atom(s) is/are in particular fluorine, chlorine and/or bromine, i.e., for example, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, heptafluoropropyl or nonafluorobutyl, in particular halomethyl, with particular preference $CH_2$—Cl, $CH(Cl)_2$, $CH_2$—F, $CHF_2$, $CF_3$, CHFCl, $CF_2$Cl or $CF(Cl)_2$, in particular $CHF_2$ or $CF_3$;

$C_1$-$C_4$-alkylthio is $SCH_3$, $SC_2H_5$, $SCH_2$—$C_2H_5$, SCH$(CH_3)_2$, n-butylthio, SCH($CH_3$)—$C_2H_5$, $SCH_2$—CH$(CH_3)_2$ or SC$(CH_3)_3$, preferably $SCH_3$ or $SC_2H_5$.

Preferred 1-methylpyrazol-4-ylcarboxanilides I are, on the one hand, those in which X is hydrogen.

On the other hand, preferred compounds I are those in which X is fluorine.

For the mixtures according to the invention, preference is given to compounds of the formula I in which $R^1$ is methyl or halomethyl, in particular $CH_3$, $CHF_2$, $CH_2F$, $CF_3$, CHFCl or $CF_2$Cl, particularly preferably $CH_3$ or $CHF_2$.

Preference is furthermore given to compounds I in which $R^2$ is hydrogen, fluorine or chlorine, in particular hydrogen or fluorine.

Preference is furthermore given to those compounds I in which $R^3$ is phenyl substituted by two or three halogen atoms, in particular 3,4-dichlorophenyl or 3,4,5-trifluorophenyl.

Moreover, preference is given to N-(3',4',5'-trifluorobiphenyl-2-yl)-3-difluoro-methyl-1-methyl-1H-pyrazole-4-carboxamide, N-[2-(1,3-dimethylbutyl)-phenyl]-1,3-dimethyl-5-fluor-1H-pyrazole-4-carboxamide (common name: Penflufen), N-(2-Bicycloprop-2-ylphenyl)-3-difluoro-methyl-1-methyl-1H-pyrazole-4-carboxamide (common name: Sedaxane), N-(trans-2-bicycloprop-2-ylphenyl)-3-difluoromethyl-1-methyl-1H-pyrazole-4-carboxamide (common name: Sedaxane; trans diastereoisomer), isopyrazam and bixafen.

Very particularly preferred are N-(3',4',5'-trifluorobiphenyl-2-yl)-3-difluoro-methyl-1-methyl-1H-pyrazole-4-carboxamide and bixafen, most preferred is N-(3',4',5'-trifluorobiphenyl-2-yl)-3-difluoro-methyl-1-methyl-1H-pyrazole-4-carboxamide (compound Ia).

With respect to the active compounds II, preference is given to mixtures of a 1-methylpyrazol-4-ylcarboxanilide I with at least one active compound II selected from the group of the A) organo(thio)phosphates, in particular acephate, chlorpyrifos, diazinon, dichlorvos, dimethoate, fenitrothion, methamidophos, methidathion, methyl-parathion, monocrotophos, phorate, profenofos or terbufos.

Very particularly preferred compounds II selected from A) are acephate, chlorpyrifos, dimethoate, methamidophos and terbufos.

Preference is also given to mixtures of a 1-methylpyrazol-4-ylcarboxanilide I with at least one active compound selected from the group of the B) carbamates, in particular aldicarb, carbaryl, carbofuran, carbosulfan, methomyl or thiodicarb.

Very particularly preferred compounds II selected from B) are aldicarb and carbofuran.

Preference is given to mixtures of a 1-methylpyrazol-4-ylcarboxanilide I with at least one active compound selected from the group of the C) pyrethroids, in particular bifenthrin, cyfluthrin, cypermethrin, alpha-cypermethrin, zeta-cypermethrin, deltamethrin, esfenvalerate, lambda-cyhalothrin, permethrin or tefluthrin.

Very particularly preferred compounds II selected from C) are bifenthrin, cypermethrin, alpha-cypermethrin, deltamethrin, lambda-cyhalothrin and tefluthrin.

Preference is furthermore also given to mixtures of a 1-methylpyrazol-4-ylcarboxanilide I with at least one active compound selected from the group of the D) growth regulators, in particular lufenuron or spirotetramat, very particularly preferred spirotetramat.

Preference is furthermore also given to mixtures of a 1-methylpyrazol-4-ylcarboxanilide I with at least one active compound selected from the group of the E) GABA antagonist compounds, in particular endosulfan.

Preference is furthermore also given to mixtures of a 1-methylpyrazol-4-ylcarboxanilide I with at least one active compound selected from the group of the F) macrocyclic lactone insecticides, in particular abamectin, emamectin, spinosad or spinetoram.

Very particularly preferred compounds II selected from F) are abamectin, spinosad and spinetoram.

Preference is furthermore also given to mixtures of a 1-methylpyrazol-4-ylcarboxanilide I with at least one active compound selected from the group of the G) METI I acaricides.

Preference is furthermore also given to mixtures of a 1-methylpyrazol-4-ylcarboxanilide I with at least one active compound selected from the group of the H) METI II and III compounds, in particular hydramethylnon.

Preference is furthermore also given to mixtures of a 1-methylpyrazol-4-ylcarboxanilide I with at least one active compound selected from the group of the J) oxidative phosphorylation inhibitor compounds, in particular fenbutatin oxide.

Preference is also given to mixtures of a 1-methylpyrazol-4-ylcarboxanilide I with at least one active compound selected from the group of the K) various compounds, in particular chlorfenapyr, cyazypyr (HGW86), cyflumetofen, flonicamid, flubendiamide, indoxacarb and metaflumizone. Very particularly preferred compounds II selected from K) are chlorfenapyr, cyazypyr (HGW86), cyflumetofen, flubendiamide and indoxacarb.

Preference is also given to three-component mixtures of one 1-methylpyrazol-4-ylcarboxanilide I with two of the active compounds II mentioned above.

Preference is also given to three-component mixtures of one compound of the formula I with two of the active compounds II mentioned above or with one active compound II and a further fungicidally active compound III selected from active compound groups L) to S):

L) Strobilurins
azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide;

M) Carboxamides
carboxanilides: benalaxyl, benalaxyl-M, benodanil, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penthiopyrad, tecloftalam, thifluzamide, tiadinil;
carboxylic morpholides: dimethomorph, flumorph;
benzoic acid amides: flumetover, fluopicolde, fluopyram, zoxamide, N-(3-ethyl-3,5,5-trimethyl-cyclohexyl)-3-formylamino-2-hydroxy-benzamide;
other carboxamides: carpropamid, dicyclomet, mandipromaid, oxytetracyclin, silthiofarm and N-(6-methoxy-pyridin-3-yl) cyclopropanecarboxylic acid amide;

N) Azoles
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;
imidazoles: cyazofamid, imazalil, pefurazoate, prochloraz, triflumizol;
benzimidazoles: benomyl, carbendazim, fuberidazole, thiabendazole;
others: ethaboxam, etridiazole, hymexazole and 2-(4-chloro-phenyl)-N-[4-(3,4-dimethoxy-phenyl)-isoxazol-5-yl]-2-prop-2-ynyloxy-acetamide;

P) Heterocyclic Compounds
pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloronicotinamide;
pyrimidines: bupirimate, cyprodinil, diflumetorim, fenarimol, ferimzone, mepanipyrim, nitrapyrin, nuarimol, pyrimethanil;
piperazines: triforine;
pyrroles: fenpiclonil, fludioxonil;
morpholines: aldimorph, dodemorph, dodemorph-acetate, fenpropimorph, tridemorph;
piperidines: fenpropidin;
dicarboximides: fluoroimid, iprodione, procymidone, vinclozolin;
non-aromatic 5-membered heterocycles: famoxadone, fenamidone, octhilinone, probenazole, 5-amino-2-isopropyl-3-oxo-4-ortho-tolyl-2,3-dihydropyrazole-1-carbothioic acid S-allyl ester;
others: acibenzolar-S-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine, 6-(3,4-dichloro-phenyl)-5-methyl-[1,2,4]triazolo[1,5-a]pyrimidine-7-ylamine, 6-(4-tert-butylphenyl)-5-methyl-[1,2,4]triazolo[1,5-a]pyrimidine-7-ylamine, 5-methyl-6-(3,5,5-trimethylhexyl)-[1,2,4]triazolo[1,5-a]pyrimidine-7-ylamine, 5-methyl-6-octyl-[1,2,4]triazolo[1,5-a]pyrimidine-7-ylamine, 6-methyl-5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethylhexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl[1,2,4]triazolo[1,5-a]pyrimidine-7-ylamine and 5-trifluoromethyl-6-(3,5,5-trimethylhexyl)-[1,2,4]triazolo[1,5-a]pyrimidine-7-ylamine;

Q) Carbamates
thio- and dithiocarbamates: ferbam, mancozeb, maneb, metam, methasulphocarb, metiram, propineb, thiram, zineb, ziram;
carbamates: benthiavalicarb, diethofencarb, flubenthiavalicarb, iprovalicarb, propamocarb, propamocarb hydrochlorid, valiphenal and N-(1-(1-(4-cyano-phenypethanesulfonyl)-but-2-yl) carbamic acid-(4-fluorophenyl) ester;

R) Other Fungicidal Active Substances
guanidines: guanidine, dodine, dodine free base, guazatine, guazatine-acetate, iminoctadine, iminoctadine-triacetate, iminoctadine-tris(albesilate);

antibiotics: kasugamycin, kasugamycin hydrochloride-hydrate, streptomycin, polyoxine, validamycin A;

nitrophenyl derivates: binapacryl, dinobuton, dinocap, nitrthal-isopropyl, tecnazen;

organometal compounds: fentin salts, such as fentin-acetate, fentin chloride or fentin hydroxide;

sulfur-containing heterocyclyl compounds: dithianon, isoprothiolane;

organophosphorus compounds: edifenphos, fosetyl, fosetyl-aluminum, iprobenfos, phosphorous acid and its salts, pyrazophos, tolclofos-methyl;

organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitrophenyl)-N-ethyl-4-methyl-benzenesulfonamide;

inorganic active substances: Bordeaux mixture, copper acetate, copper hydroxide, copper oxychloride, basic copper sulfate, sulfur;

others: biphenyl, bronopol, cyflufenamid, cymoxanil, diphenylamin, metrafenone, mildiomycin, oxin-copper, prohexadione-calcium, spiroxamine, tolylfluanid, N-(cyclopropylmethoxyimino-(6-difluoro-methoxy-2, 3-difluorophenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine and N'-(5-difluoromethyl-2-methyl-4-(3-trimethylsilanyl-propoxy)-phenyl)-N-ethyl-N-methyl formamidine.

S) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

The active compounds III mentioned above, their preparation and their action against harmful fungi are generally known (cf., for example, http://www.hclrss.demon.co.uk/index.html); they are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325, 503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

Preference is also given to three-component mixtures comprising a compound I (component 1) and at least one active substance II selected from the strobilurines of group L) (component 2) and particularly selected from azoxystrobin, dimoxystrobin, fluoxastrobin, kresoxim-methyl, orysastrobin, picoxystrobin, pyraclostrobin and trifloxystrobin.

Preference is also given to three-component mixtures comprising a compound I (component 1) and at least one active substance II selected from the carboxamides of group M) (component 2) and particularly selected from fenhexamid, metalaxyl, mefenoxam, ofurace, dimethomorph, flumorph, fluopicolid (picobenzamid), zoxamide, carpropamid and mandipropamid.

Preference is given to three-component mixtures comprising a compound of formula I (component 1) and at least one active substance II selected from the azoles of group N) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, cyazofamid, benomyl, carbendazim and ethaboxam.

Preference is also given to three-component mixtures comprising a compound I (component 1) and at least one active substance II selected from the heterocyclic compounds of group P) (component 2) and particularly selected from fluazinam, cyprodinil, fenarimol, mepanipyrim, pyrimethanil, triforine, fludioxonil, dodemorph, fenpropimorph, tridemorph, fenpropidin, iprodione, vinclozolin, famoxadone, fenamidone, probenazole, proquinazid, acibenzolar-S-methyl, captafol, folpet, fenoxanil and quinoxyfen.

Preference is also given to three-component mixtures comprising a compound I (component 1) and at least one active substance II selected from the carbamates of group Q) (component 2) and particularly selected from mancozeb, metiram, propineb, thiram, iprovalicarb, flubenthiavalicarb and propamocarb.

Preference is also given to three-component mixtures comprising a compound I (component 1) and at least one active substance II selected from the fungicides given in group R) (component 2) and particularly selected from dithianon, fentin salts, such as fentin acetate, fosetyl, fosetyl-aluminium, $H_3PO_3$ and salts thereof, chlorthalonil, dichlofluanid, thiophanat-methyl, copper acetate, copper hydroxide, copper oxychloride, copper sulfate, sulfur, cymoxanil, metrafenone, spiroxamine and 5-chloro-7-(4-methylpiperidin-1-yl)-6-(2, 4,6-trifluorophenyl)-[1,2,4]-triazolo[1,5-a]pyrimidine.

Preference is also given to four-component mixtures of compounds I and II with two further active compounds selected from compounds II and III mentioned above.

Preferred active compound combinations are listed in tables 1 to 9 below:

TABLE 1

Active compound combinations of compounds I with active compounds II of group A):

| Mixture | Compound I | Compound II |
|---------|-----------|-------------|
| No. A.1 | N-(3',4',5'-trifluorobiphenyl-2-yl)-3-difluoro-methyl-1-methyl-1H-pyrazole-4-carboxamide | acephate |
| No. A.2 | N-[2-(1,3-dimethylbutyl)-phenyl]-1,3-dimethyl-5-fluor-1H-pyrazole-4-carboxamide | acephate |
| No. A.3 | N-(trans-2-bicycloprop-2-ylphenyl)-3-difluoro-methyl-1-methyl-1H-pyrazole-4-carboxamide | acephate |
| No. A.4 | isopyrazam | acephate |
| No. A.5 | bixafen | acephate |

TABLE 1-continued

Active compound combinations of compounds I with active compounds II of group A):

| Mixture | Compound I | Compound II |
|---|---|---|
| No. A.6 | N-(3',4',5'-trifluorobiphenyl-2-yl)-3-difluoro-methyl-1-methyl-1H-pyrazole-4-carboxamide | chlorpyrifos |
| No. A.7 | N-[2-(1,3-dimethylbutyl)-phenyl]-1,3-dimethyl-5-fluor-1H-pyrazole-4-carboxamide | chlorpyrifos |
| No. A.8 | N-(trans-2-bicycloprop-2-ylphenyl)-3-difluoro-methyl-1-methyl-1H-pyrazole-4-carboxamide | chlorpyrifos |
| No. A.9 | isopyrazam | chlorpyrifos |
| No. A.10 | bixafen | chlorpyrifos |
| No. A.11 | N-(3',4',5'-trifluorobiphenyl-2-yl)-3-difluoro-methyl-1-methyl-1H-pyrazole-4-carboxamide | dimethoate, |
| No. A.12 | N-[2-(1,3-dimethylbutyl)-phenyl]-1,3-dimethyl-5-fluor-1H-pyrazole-4-carboxamide | dimethoate, |
| No. A.13 | N-(trans-2-bicycloprop-2-ylphenyl)-3-difluoro-methyl-1-methyl-1H-pyrazole-4-carboxamide | dimethoate, |
| No. A.14 | isopyrazam | dimethoate, |
| No. A.15 | bixafen | dimethoate, |
| No. A.16 | N-(3',4',5'-trifluorobiphenyl-2-yl)-3-difluoro-methyl-1-methyl-1H-pyrazole-4-carboxamide | methamidophos |
| No. A.17 | N-[2-(1,3-dimethylbutyl)-phenyl]-1,3-dimethyl-5-fluor-1H-pyrazole-4-carboxamide | methamidophos |
| No. A.18 | N-(trans-2-bicycloprop-2-ylphenyl)-3-difluoro-methyl-1-methyl-1H-pyrazole-4-carboxamide | methamidophos |
| No. A.19 | isopyrazam | methamidophos |
| No. A.20 | bixafen | methamidophos |
| No. A.21 | N-(3',4',5'-trifluorobiphenyl-2-yl)-3-difluoro-methyl-1-methyl-1H-pyrazole-4-carboxamide | terbufos |
| No. A.22 | N-[2-(1,3-dimethylbutyl)-phenyl]-1,3-dimethyl-5-fluor-1H-pyrazole-4-carboxamide | terbufos |
| No. A.23 | N-(trans-2-bicycloprop-2-ylphenyl)-3-difluoro-methyl-1-methyl-1H-pyrazole-4-carboxamide | terbufos |
| No. A.24 | isopyrazam | terbufos |
| No. A.25 | bixafen | terbufos |

TABLE 2

Active compound combinations of compounds I with active compounds II of group B):

| Mixture | Compound I | Compound II |
|---|---|---|
| No. B.1 | N-(3',4',5'-trifluorobiphenyl-2-yl)-3-difluoro-methyl-1-methyl-1H-pyrazole-4-carboxamide | aldicarb |
| No. B.2 | N-[2-(1,3-dimethylbutyl)-phenyl]-1,3-dimethyl-5-fluor-1H-pyrazole-4-carboxamide | aldicarb |
| No. B.3 | N-(trans-2-bicycloprop-2-ylphenyl)-3-difluoro-methyl-1-methyl-1H-pyrazole-4-carboxamide | aldicarb |
| No. B.4 | isopyrazam | aldicarb |
| No. B.5 | bixafen | aldicarb |
| No. B.6 | N-(3',4',5'-trifluorobiphenyl-2-yl)-3-difluoro-methyl-1-methyl-1H-pyrazole-4-carboxamide | carbofuran |
| No. B.7 | N-[2-(1,3-dimethylbutyl)-phenyl]-1,3-dimethyl-5-fluor-1H-pyrazole-4-carboxamide | carbofuran |
| No. B.8 | N-(trans-2-bicycloprop-2-ylphenyl)-3-difluoro-methyl-1-methyl-1H-pyrazole-4-carboxamide | carbofuran |
| No. B.9 | isopyrazam | carbofuran |
| No. B.10 | bixafen | carbofuran |

TABLE 3

Active compound combinations of compounds I with active compounds II of group C):

| Mixture | Compound I | Compound II |
|---|---|---|
| No. C.1 | N-(3',4',5'-trifluorobiphenyl-2-yl)-3-difluoro-methyl-1-methyl-1H-pyrazole-4-carboxamide | bifenthrin |
| No. C.2 | N-[2-(1,3-dimethylbutyl)-phenyl]-1,3-dimethyl-5-fluor-1H-pyrazole-4-carboxamide | bifenthrin |
| No. C.3 | N-(trans-2-bicycloprop-2-ylphenyl)-3-difluoro-methyl-1-methyl-1H-pyrazole-4-carboxamide | bifenthrin |
| No. C.4 | isopyrazam | bifenthrin |
| No. C.5 | bixafen | bifenthrin |
| No. C.6 | N-(3',4',5'-trifluorobiphenyl-2-yl)-3-difluoro-methyl-1-methyl-1H-pyrazole-4-carboxamide | cypermethrin |
| No. C.7 | N-[2-(1,3-dimethylbutyl)-phenyl]-1,3-dimethyl-5-fluor-1H-pyrazole-4-carboxamide | cypermethrin |
| No. C.8 | N-(trans-2-bicycloprop-2-ylphenyl)-3-difluoro-methyl-1-methyl-1H-pyrazole-4-carboxamide | cypermethrin |
| No. C.9 | isopyrazam | cypermethrin |
| No. C.10 | bixafen | cypermethrin |
| No. C.11 | N-(3',4',5'-trifluorobiphenyl-2-yl)-3-difluoro-methyl-1-methyl-1H-pyrazole-4-carboxamide | alpha-cypermethrin |
| No. C.12 | N-[2-(1,3-dimethylbutyl)-phenyl]-1,3-dimethyl-5-fluor-1H-pyrazole-4-carboxamide | alpha-cypermethrin |
| No. C.13 | N-(trans-2-bicycloprop-2-ylphenyl)-3-difluoro-methyl-1-methyl-1H-pyrazole-4-carboxamide | alpha-cypermethrin |
| No. C.14 | isopyrazam | alpha-cypermethrin |
| No. C.15 | bixafen | alpha-cypermethrin |
| No. C.16 | N-(3',4',5'-trifluorobiphenyl-2-yl)-3-difluoro-methyl-1-methyl-1H-pyrazole-4-carboxamide | deltamethrin |
| No. C.17 | N-[2-(1,3-dimethylbutyl)-phenyl]-1,3-dimethyl-5-fluor-1H-pyrazole-4-carboxamide | deltamethrin |
| No. C.18 | N-(trans-2-bicycloprop-2-ylphenyl)-3-difluoro-methyl-1-methyl-1H-pyrazole-4-carboxamide | deltamethrin |
| No. C.19 | isopyrazam | deltamethrin |
| No. C.20 | bixafen | deltamethrin |
| No. C.21 | N-(3',4',5'-trifluorobiphenyl-2-yl)-3-difluoro-methyl-1-methyl-1H-pyrazole-4-carboxamide | lambda-cyhalothrin |
| No. C.22 | N-[2-(1,3-dimethylbutyl)-phenyl]-1,3-dimethyl-5-fluor-1H-pyrazole-4-carboxamide | lambda-cyhalothrin |
| No. C.23 | N-(trans-2-bicycloprop-2-ylphenyl)-3-difluoro-methyl-1-methyl-1H-pyrazole-4-carboxamide | lambda-cyhalothrin |
| No. C.24 | isopyrazam | lambda-cyhalothrin |
| No. C.25 | bixafen | lambda-cyhalothrin |
| No. C.26 | N-(3',4',5'-trifluorobiphenyl-2-yl)-3-difluoro-methyl-1-methyl-1H-pyrazole-4-carboxamide | tefluthrin |
| No. C.27 | N-[2-(1,3-dimethylbutyl)-phenyl]-1,3-dimethyl-5-fluor-1H-pyrazole-4-carboxamide | tefluthrin |
| No. C.28 | N-(trans-2-bicycloprop-2-ylphenyl)-3-difluoro-methyl-1-methyl-1H-pyrazole-4-carboxamide | tefluthrin |
| No. C.29 | isopyrazam | tefluthrin |
| No. C.30 | bixafen | tefluthrin |

TABLE 4

Active compound combinations of compounds I with active compounds II of group D):

| Mixture | Compound I | Compound II |
|---|---|---|
| No. D.1 | N-(3',4',5'-trifluorobiphenyl-2-yl)-3-difluoro-methyl-1-methyl-1H-pyrazole-4-carboxamide | spirotetramat |

TABLE 4-continued

Active compound combinations of compounds I with active compounds II of group D):

| Mixture | Compound I | Compound II |
|---|---|---|
| No. D.2 | N-[2-(1,3-dimethylbutyl)-phenyl]-1,3-dimethyl-5-fluor-1H-pyrazole-4-carboxamide | spirotetramat |
| No. D.3 | N-(trans-2-bicycloprop-2-ylphenyl)-3-difluoro-methyl-1-methyl-1H-pyrazole-4-carboxamide | spirotetramat |
| No. D.4 | isopyrazam | spirotetramat |
| No. D.5 | bixafen | spirotetramat |

TABLE 5

Active compound combinations of compounds I with active compounds II of group E):

| Mixture | Compound I | Compound II |
|---|---|---|
| No. E.1 | N-(3',4',5'-trifluorobiphenyl-2-yl)-3-difluoro-methyl-1-methyl-1H-pyrazole-4-carboxamide | endosulfan |
| No. E.2 | N-[2-(1,3-dimethylbutyl)-phenyl]-1,3-dimethyl-5-fluor-1H-pyrazole-4-carboxamide | endosulfan |
| No. E.3 | N-(trans-2-bicycloprop-2-ylphenyl)-3-difluoro-methyl-1-methyl-1H-pyrazole-4-carboxamide | endosulfan |
| No. E.4 | isopyrazam | endosulfan |
| No. E.5 | bixafen | endosulfan |

TABLE 6

Active compound combinations of compounds I with active compounds II of group F):

| Mixture | Compound I | Compound II |
|---|---|---|
| No. F.1 | N-(3',4',5'-trifluorobiphenyl-2-yl)-3-difluoro-methyl-1-methyl-1H-pyrazole-4-carboxamide | abamectin, and |
| No. F.2 | N-[2-(1,3-dimethylbutyl)-phenyl]-1,3-dimethyl-5-fluor-1H-pyrazole-4-carboxamide | abamectin |
| No. F.3 | N-(trans-2-bicycloprop-2-ylphenyl)-3-difluoro-methyl-1-methyl-1H-pyrazole-4-carboxamide | abamectin |
| No. F.4 | isopyrazam | abamectin |
| No. F.5 | bixafen | abamectin |
| No. F.6 | N-(3',4',5'-trifluorobiphenyl-2-yl)-3-difluoro-methyl-1-methyl-1H-pyrazole-4-carboxamide | spinosad |
| No. F.7 | N-[2-(1,3-dimethylbutyl)-phenyl]-1,3-dimethyl-5-fluor-1H-pyrazole-4-carboxamide | spinosad |
| No. F.8 | N-(trans-2-bicycloprop-2-ylphenyl)-3-difluoro-methyl-1-methyl-1H-pyrazole-4-carboxamide | spinosad |
| No. F.9 | isopyrazam | spinosad |
| No. F.10 | bixafen | spinosad |
| No. F.11 | N-(3',4',5'-trifluorobiphenyl-2-yl)-3-difluoro-methyl-1-methyl-1H-pyrazole-4-carboxamide | spinetoram |
| No. F.12 | N-[2-(1,3-dimethylbutyl)-phenyl]-1,3-dimethyl-5-fluor-1H-pyrazole-4-carboxamide | spinetoram |
| No. F.13 | N-(trans-2-bicycloprop-2-ylphenyl)-3-difluoro-methyl-1-methyl-1H-pyrazole-4-carboxamide | spinetoram |
| No. F.14 | isopyrazam | spinetoram |
| No. F.15 | bixafen | spinetoram |

TABLE 7

Active compound combinations of compounds I with active compounds II of group H):

| Mixture | Compound I | Compound II |
|---|---|---|
| No. H.1 | N-(3',4',5'-trifluorobiphenyl-2-yl)-3-difluoro-methyl-1-methyl-1H-pyrazole-4-carboxamide | hydramethylnon |
| No. H.2 | N-[2-(1,3-dimethylbutyl)-phenyl]-1,3-dimethyl-5-fluor-1H-pyrazole-4-carboxamide | hydramethylnon |
| No. H.3 | N-(trans-2-bicycloprop-2-ylphenyl)-3-difluoro-methyl-1-methyl-1H-pyrazole-4-carboxamide | hydramethylnon |
| No. H.4 | isopyrazam | hydramethylnon |
| No. H.5 | bixafen | hydramethylnon |

TABLE 8

Active compound combinations of compounds I with active compounds II of group J):

| Mixture | Compound I | Compound II |
|---|---|---|
| No. J.1 | N-(3',4',5'-trifluorobiphenyl-2-yl)-3-difluoro-methyl-1-methyl-1H-pyrazole-4-carboxamide | fenbutatin oxide |
| No. J.2 | N-[2-(1,3-dimethylbutyl)-phenyl]-1,3-dimethyl-5-fluor-1H-pyrazole-4-carboxamide | fenbutatin oxide |
| No. J.3 | N-(trans-2-bicycloprop-2-ylphenyl)-3-difluoro-methyl-1-methyl-1H-pyrazole-4-carboxamide | fenbutatin oxide |
| No. J.4 | isopyrazam | fenbutatin oxide |
| No. J.5 | bixafen | fenbutatin oxide |

TABLE 9

Active compound combinations of compounds I with active compounds II of group K):

| Mixture | Compound I | Compound II |
|---|---|---|
| No. K.1 | N-(3',4',5'-trifluorobiphenyl-2-yl)-3-difluoro-methyl-1-methyl-1H-pyrazole-4-carboxamide | chlorfenapyr |

TABLE 9-continued

Active compound combinations of compounds
I with active compounds II of group K):

| Mixture | Compound I | Compound II |
|---|---|---|
| No. K.2 | N-[2-(1,3-dimethylbutyl)-phenyl]-1,3-dimethyl-5-fluor-1H-pyrazole-4-carboxamide | chlorfenapyr |
| No. K.3 | N-(trans-2-bicycloprop-2-ylphenyl)-3-difluoromethyl-1-methyl-1H-pyrazole-4-carboxamide | chlorfenapyr |
| No. K.4 | isopyrazam | chlorfenapyr |
| No. K.5 | bixafen | chlorfenapyr |
| No. K.6 | N-(3',4',5'-trifluorobiphenyl-2-yl)-3-difluoromethyl-1-methyl-1H-pyrazole-4-carboxamide | cyazypyr (HGW86) |
| No. K.7 | N-[2-(1,3-dimethylbutyl)-phenyl]-1,3-dimethyl-5-fluor-1H-pyrazole-4-carboxamide | cyazypyr (HGW86) |
| No. K.8 | N-(trans-2-bicycloprop-2-ylphenyl)-3-difluoromethyl-1-methyl-1H-pyrazole-4-carboxamide | cyazypyr (HGW86) |
| No. K.9 | isopyrazam | cyazypyr (HGW86) |
| No. K.10 | bixafen | cyazypyr (HGW86) |
| No. K.11 | N-(3',4',5'-trifluorobiphenyl-2-yl)-3-difluoromethyl-1-methyl-1H-pyrazole-4-carboxamide | cyflumetofen |
| No. K.12 | N-[2-(1,3-dimethylbutyl)-phenyl]-1,3-dimethyl-5-fluor-1H-pyrazole-4-carboxamide | cyflumetofen |
| No. K.13 | N-(trans-2-bicycloprop-2-ylphenyl)-3-difluoromethyl-1-methyl-1H-pyrazole-4-carboxamide | cyflumetofen |
| No. K.14 | isopyrazam | cyflumetofen |
| No. K.15 | bixafen | cyflumetofen |
| No. K.16 | N-(3',4',5'-trifluorobiphenyl-2-yl)-3-difluoromethyl-1-methyl-1H-pyrazole-4-carboxamide | flubendiamide |
| No. K.17 | N-[2-(1,3-dimethylbutyl)-phenyl]-1,3-dimethyl-5-fluor-1H-pyrazole-4-carboxamide | flubendiamide |
| No. K.18 | N-(trans-2-bicycloprop-2-ylphenyl)-3-difluoromethyl-1-methyl-1H-pyrazole-4-carboxamide | flubendiamide |
| No. K.19 | isopyrazam | flubendiamide |
| No. K.20 | bixafen | flubendiamide |
| No. K.21 | N-(3',4',5'-trifluorobiphenyl-2-yl)-3-difluoromethyl-1-methyl-1H-pyrazole-4-carboxamide | indoxacarb |
| No. K.22 | N-[2-(1,3-dimethylbutyl)-phenyl]-1,3-dimethyl-5-fluor-1H-pyrazole-4-carboxamide | indoxacarb |
| No. K.23 | N-(trans-2-bicycloprop-2-ylphenyl)-3-difluoromethyl-1-methyl-1H-pyrazole-4-carboxamide | indoxacarb |
| No. K.24 | isopyrazam | indoxacarb |
| No. K.25 | bixafen | indoxacarb |
| No. K.26 | N-(3',4',5'-trifluorobiphenyl-2-yl)-3-difluoromethyl-1-methyl-1H-pyrazole-4-carboxamide | metaflumizone |
| No. K.27 | N-[2-(1,3-dimethylbutyl)-phenyl]-1,3-dimethyl-5-fluor-1H-pyrazole-4-carboxamide | metaflumizone |
| No. K.28 | N-(trans-2-bicycloprop-2-ylphenyl)-3-difluoromethyl-1-methyl-1H-pyrazole-4-carboxamide | metaflumizone |
| No. K.29 | isopyrazam | metaflumizone |
| No. K.30 | bixafen | metaflumizone |

The mixtures of active substances can be prepared as compositions comprising besides the active compounds at least one inert ingredient by usual means, e.g. by the means given for the compositions of compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn. Oomycetes). In addition, it is referred to the explanations regarding the fungicidal activity of the compounds and the compositions containing compounds I, respectively.

The mixtures of the compound(s) I with at least one of the active compounds II, or the simultaneous, that is joint or separate, use of a compound I with at least one of the active compounds II, are/is distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants The compounds I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or goose-berries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grape-fruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e. g. conifers; and on the plant propagation material, such as seeds, and the crop material of these plants.

Preferably, compounds I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e.g. EP-A 242 236, EP-A 242 246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato Solanum bulbocastanum) or T4-lysozym (e. g. potato cultivars capable of synthesizing these proteins with increased resistance against bacteria such as Erwinia amylvora). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The compounds I and compositions thereof, respectively, are particularly suitable for controlling the following plant diseases:

*Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternate*), tomatoes (e. g. *A. solani* or *A. alternate*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.) on corn (e. g. *D. maydis*), cereals (e. g. *B. sorokiniana*: spot blotch), rice (e. g. *B. oryzae*) and turfs; *Blumeria* (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn, rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (*anthracnose*) on cotton (e. g. *C. gossypii*), corn (e. g. *C. graminicola*), soft fruits, potatoes (e. g. *C. coccodes*: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; *Dematophora* (teleomorph: *Rosellinia*) *necatrix* (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; *Esca* (*dieback, apoplexy*) on vines, caused by *Formitiporia* (syn. *Phellinus*) *punctata, F. mediterranea, Phaeomoniella chlamydospora* (earlier *Phaeoacremonium chlamydosporum*), *Phaeoacremonium aleophilum* and/or *Botryosphaeria obtusa; Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e. g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph:

*Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, and asparagus (e. g. *P. asparagi*); *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria blotch*) on wheat and *S.* (syn. *Stagonospora*) *nodorum* (*Stagonospora blotch*) on cereals; *Uncinula* (syn. *Erysiphe*) *necator* (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora blotch*, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and compositions thereof, respectively, are also suitable for controlling harmful fungi in the protection of materials (e. g. wood, paper, paint dispersions, fiber or fabrics) and in the protection of stored products. As to the protection of wood and construction materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products the following yeast fungi are worthy of note: *Candida* spp. and *Saccharomyces cerevisae*.

Application of the inventive combinations to useful plants may also lead to an increase in the crop yield.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with a composition comprising at least one compound I prophylactically either at or before planting or transplanting.

The invention also relates to agrochemical compositions comprising a solvent or solid carrier and at least one compound I and to the use for controlling harmful fungi.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

Compounds I, II and optionally III can be converted into customary types of agrochemical compositions, e. g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e. g. SC, OD, FS, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. No. 4,172,714, U.S. Pat. No. 4,144, 050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e. g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e. g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e. g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as lignin-soulfonic acid (Borresperse® types, Borregard, Norway) phenolsulfonic acid, naphthalenesulfonic acid (Morwet® types, Akzo Nobel, U.S.A.), dibutylnaphthalenesulfonic acid (Nekal® types, BASF, Germany),and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers therof.

Examples for thickeners (i. e. compounds that impart a modified flowability to compositions, i. e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e. g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and, if appropriate, further active substances, with at least one solid carrier.

Granules, e. g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e. g., ammonium sulfate, ammonium phosphate, ammonium nitrate, ureas, and products of vegetable origin, such as cereal meal, tree bark meal, wood meal and nutshell meal, cellulose powders and other solid carriers.

Examples for composition types are:
1. Composition Types for Dilution with Water
 i) Water-Soluble Concentrates (SL, LS)
 10 parts by weight of the active compound(s) according to the invention are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.
 ii) Dispersible Concentrates (DC)
 20 parts by weight of the active compound(s) according to the invention are dissolved in 70 parts by weight of cyclohexanone with addition of 10 parts by weight of a dispersant, e. g.

polyvinylpyrrolidone. Dilution with water gives a dispersion. The active substance content is 20% by weight.

iii) Emulsifiable Concentrates (EC)

15 parts by weight of the active compound(s) according to the invention are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of the active compound(s) according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of the active compound(s) according to the invention are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of the active compound(s) according to the invention are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of the active compound(s) according to the invention are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of the active compound(s) according to the invention are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted ix) Dustable Powders (DP, DS)

5 parts by weight of the active compound(s) according to the invention are ground finely and mixed intimately with 95 parts by weight of finely divided kaolin. This gives a dustable composition having an active substance content of 5% by weight.

x) Granules (GR, FG, GG, MG)

0.5 parts by weight of the active compound(s) according to the invention is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of the active compound(s) according to the invention are dissolved in 90 parts by weight of an organic solvent, e.g. xylene. This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before sowing. Methods for applying or treating agrochemical compounds and compositions thereof, respectively, on to plant propagation material, especially seeds, are known in the art, and include dressing, coating, pelleting, dusting and soaking application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts applied are, depending on the kind of effect desired, between 0.01 and 2.0 kg of active substance per ha.

In treatment of plant propagation materials such as seeds, e. g. by dusting, coating or drenching seed, amounts of active substance of from 1 to 1000 g, preferably from 5 to 100 g, per 100 kilogram of seed are generally required.

When used in the protection of materials or stored products, the amount of active substance applied depends on the kind of application area and on the desired effect. Amounts customarily applied in the protection of materials are, e. g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e. g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e. g. with herbicides, insecticides, growth regulators, fungicides or else with fertilizers, as pre-mix or, if appropriate, not until immediately prior to use (tank mix).

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Oils of various types, wetting agents or adjuvants may be added to the active compounds, even, if appropriate, not until immediately prior to use (tank mix). These agents are typically admixed with the compositions according to the invention in a weight ratio of from 1:100 to 100:1, preferably from 1:10 to 10:1.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol ON 30®; EO/PO block polymers, for example Pluronic RPE 2035® and Genapol B®; alcohol ethoxylates, for example Lutensol XP 80®; and sodium dioctylsulfosuccinate, for example Leophen RA®.

The compounds I and II or the mixtures or the corresponding formulations are applied by treating the harmful fungi, the plants, seeds, soils, areas, materials or spaces to be kept free from them with a fungicidally effective amount of the mixture or, in the case of separate application, of the compounds I and II. Application can be before or after the infection by harmful fungi.

The fungicidal action of the individual compounds and of the synergistically active mixtures according to the invention was demonstrated by the tests below.

A) Microtiter Tests

The active compounds were formulated separately as a stock solution having a concentration of 10000 ppm in dimethyl sulfoxide. The products dimethoate, deltamethrin, lambda-cyalothrin, abamectin, hydromethylnon, fenbutadinoxyd and indoxacarb were used as commercial finished formulations and diluted with water to the stated concentration of the active compound. The measured parameters were compared to the growth of the active compound-free control variant (100%) and the fungus-free and active compound-free blank value to determine the relative growth in % of the pathogens in the respective active compounds. These percentages were converted into efficacies.

An efficacy of 0 means that the growth level of the pathogens corresponds to that of the untreated control; an efficacy of 100 means that the pathogens were not growing.

The expected efficacies of active compound mixtures were determined using Colby's formula (Colby, S. R. "Calculating synergistic and antagonistic responses of herbicide combinations", Weeds, 15, pp. 20-22, 1967) and compared with the observed efficacies.

Colby's Formula:

$$E = x + y - x \cdot y / 100$$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b

USE EXAMPLE 1

Activity Against the Late Blight Pathogen
*Phytophthora infestans*

The stock solutions were mixed according to the ratio, pipetted onto a micro titer plate (MTP) and diluted with water to the stated concentrations. A zoospore suspension of *Phytophthora infestans* in an aqueous pea juice solution was then added. The plates were placed in a water vapor-saturated chamber at temperatures of 18° C. Using an absorption photometer, the MTPs were measured at 405 nm on day 7 after the inoculation. The measured parameters were compared to the growth of the active substance-free control variant (=100%)

and the fungus- and active substance-free blank value to determine the relative growth in % of the pathogens in the individual active substances.

USE EXAMPLE 2

Activity Against the Rice Blast Pathogen Caused by *Pyricularia oryzae*

The stock solutions were mixed according to the ratio, pipetted onto a micro titer plate (MTP) and diluted with water to the stated concentrations. A spore suspension of *Pyricularia oryzae* in an aqueous biomalt solution was then added. The plates were placed in a water vapor-saturated chamber at temperatures of 18° C. Using an absorption photometer, the microtiter plates were measured at 405 nm on day 7 after the inoculation. The measured parameters were compared to the growth of the active substance-free control variant (=100%) and the fungus- and active substance-free blank value to determine the relative growth in % of the pathogens in the individual active substances.

TABLE 10

| Active compounds/ active compound mixture | Concentration [ppm] | Ratio | Observed efficacy | Calculated efficacy according to Colby (%) |
|---|---|---|---|---|
| Ia = N-(3',4',5'-trifluorobiphenyl-2-yl)-3-difluoromethyl-1-methyl-1H-pyrazole-4-carboxamide | 0.004 | — | 3 | — |
| Bixafen | 0.25 | — | 6 | — |
|  | 0.063 | — | 6 | — |
| Isopyrazam | 0.016 | — | 15 | — |
| Penflufen | 0.25 | — | 5 | — |
| Sedaxane (trans diastereoisomer) | 0.016 | — | 1 | — |
| Indoxacarb | 1 | — | 0 | — |
| alpha-Cypermethrin | 63 | — | 41 | — |
| Endosulfan | 63 | — | 73 | — |
|  | 16 | — | 22 | — |
| Chlorfenapyr | 63 | — | 38 | — |
|  | 4 | — | 17 | — |
| Flubendiamid | 63 | — | 15 | — |
|  | 4 | — | 0 | — |
| Deltamethrin | 4 | — | 0 | — |
| Hydramethylnon | 4 | — | 5 | — |
| Fenbutadin-oxyd | 4 | — | 39 | — |
| Ia + Indoxacarb | 0.004 + 1 | 1:250 | 35 | 3 |
| Bixafen + alpha-Cypermethrin | 0.25 + 63 | 1:250 | 63 | 44 |
| Bixafen + Endosulfan | 0.063 + 16 | 1:250 | 82 | 26 |
| Bixafen + Chlorfenapyr | 0.25 + 63 | 1:250 | 87 | 42 |
| Bixafen + Flubendiamid | 0.25 + 63 | 1:250 | 100 | 20 |
| Isopyrazam + Deltamethrin | 0.016 + 4 | 1:250 | 64 | 15 |
| Isopyrazam + Hydramethylon | 0.016 + 4 | 1:250 | 43 | 19 |
| Isopyrazam + Chlorfenapyr | 0.016 + 4 | 1:250 | 83 | 30 |
| Isopyrazam + Flubendiamid | 0.016 + 4 | 1:250 | 48 | 15 |
| Penflufen + Endosulfan | 0.25 + 63 | 1:250 | 100 | 74 |
| Sedaxane (trans stereoisomer) + Fenbutadin-oxyd | 0.016 + 4 | 1:250 | 65 | 40 |

USE EXAMPLE 3

Activity Against Leaf Blotch on Wheat Caused by *Septoria tritici*

The stock solutions were mixed according to the ratio, pipetted onto a micro titer plate (MTP) and diluted with water to the stated concentrations. A spore suspension of *Septoria tritici* in an aqueous biomalt solution was then added. The plates were placed in a water vapor-saturated chamber at temperatures of 18° C. Using an absorption photometer, the microtiter plates were measured at 405 nm on day 7 after the inoculation. The measured parameters were compared to the growth of the active substance-free control variant (=100%) and the fungus- and active substance-free blank value to determine the relative growth in % of the pathogens in the individual active substances.

TABLE 11

| Active compounds/ active compound mixture | Concentration [ppm] | Ratio | Observed efficacy | Calculated efficacy according to Colby (%) |
|---|---|---|---|---|
| Ia | 0.016 | — | 29 | — |
| Bixafen | 0.063 | — | 48 | — |
| Isopyrazam | 0.063 | — | 58 | — |
| Penflufen | 0.25 | — | 44 | — |
| Sedaxane (trans diastereoisomer) | 0.25 | — | 57 | — |
| Acephate | 4 | — | 2 | — |
| Dimethoate | 4 | — | 2 | — |
| Methamidophos | 4 | — | 5 | — |
| Deltamethrin | 63 | — | 3 | — |
|  | 16 | — | 0 | — |
| Endosulfan | 63 | — | 26 | — |
|  | 16 | — | 3 | — |
| Hydramethylnon | 63 | — | 4 | — |
|  | 16 | — | 0 | — |
| Chlorfenapyr | 16 | — | 8 | — |
| Indoxacarb | 63 | — | 19 | — |
|  | 16 | — | 9 | — |
| Terbufos | 16 | — | 14 | — |
| Aldicarb | 16 | — | 7 | — |
| lambda-Cyalothrin | 63 | — | 29 | — |
|  | 16 | — | 10 | — |
| Flubendiamid | 63 | — | 37 | — |
| Ia + Acephate | 0.016 + 4 | 1:250 | 73 | 30 |
| Ia + Dimethoate | 0.016 + 4 | 1:250 | 49 | 30 |
| Ia + Methamidophos | 0.016 + 4 | 1:250 | 68 | 32 |
| Bixafen + Deltamethrin | 0.063 + 16 | 1:250 | 95 | 48 |
| Bixafen + Endosulfan | 0.063 + 16 | 1:250 | 96 | 49 |
| Bixafen + Hydramethylnon | 0.063 + 16 | 1:250 | 71 | 48 |
| Bixafen + Chlorfenapyr | 0.063 + 16 | 1:250 | 71 | 52 |
| Bixafen + Indoxacarb | 0.063 + 16 | 1:250 | 78 | 52 |
| Isopyrazam + Terbufos | 0.063 + 16 | 1:250 | 91 | 64 |
| Isopyrazam + Aldicarb | 0.063 + 16 | 1:250 | 82 | 61 |
| Isopyrazam + Deltamethrin | 0.063 + 16 | 1:250 | 80 | 58 |
| Isopyrazam + lambda-Cyalothrin | 0.063 + 16 | 1:250 | 85 | 62 |
| Isopyrazam + Endosulfan | 0.063 + 16 | 1:250 | 100 | 60 |
| Isopyrazam + Hydramethylnon | 0.063 + 16 | 1:250 | 89 | 58 |
| Isopyrazam + Chlorfenapyr | 0.63 + 16 | 1:250 | 83 | 62 |
| Isopyrazam + Indoxacarb | 0.063 + 16 | 1:250 | 83 | 62 |

TABLE 11-continued

| Active compounds/active compound mixture | Concentration [ppm] | Ratio | Observed efficacy | Calculated efficacy according to Colby (%) |
|---|---|---|---|---|
| Penflufen + Deltamethrin | 0.25 + 63 | 1:250 | 100 | 46 |
| Penflufen + Endosulfan | 0.25 + 63 | 1:250 | 97 | 58 |
| Penflufen + Hydramethylnon | 0.25 + 63 | 1:250 | 76 | 46 |
| Penflufen + Indoxacarb | 0.25 + 63 | 1:250 | 75 | 54 |
| Sedaxane + Deltamethrin | 0.25 + 63 | 1:250 | 90 | 59 |
| Sedaxane + lambda-Cyalothrin | 0.25 + 63 | 1:250 | 89 | 67 |
| Sedaxane + Endosulfan | 0.25 + 63 | 1:250 | 100 | 68 |
| Sedaxane + Flubendiamid | 0.25 + 63 | 1:250 | 100 | 73 |

USE EXAMPLE 4

Activity Against *Alternaria solani*

The stock solutions were mixed according to the ratio, pipetted onto a micro titer plate (MTP) and diluted with water to the stated concentrations. A spore suspension of *Alternaria solani* in an aqueous biomalt solution was then added. The plates were placed in a water vapor-saturated chamber at a temperature of 18° C. Using an absorption photometer, the MTPs were measured at 405 nm 7 days after the inoculation.

TABLE 12

| Active compounds/active compound mixture | Concentration [ppm] | Ratio | Observed efficacy | Calculated efficacy according to Colby (%) |
|---|---|---|---|---|
| Ia | 0.004 | — | 29 | — |
| Bixafen | 0.004 | — | 0 | — |
| Isopyrazam | 0.016 | — | 2 | — |
| Penflufen | 0.063 | — | 0 | — |
| Sedaxane (trans diastereoisomer) | 0.25 | — | 20 | — |
| | 0.063 | — | 0 | — |
| Acephate | 1 | — | 3 | — |
| Methamidophos | 63 | — | 0 | — |
| | 1 | — | 8 | — |
| Deltamethrin | 16 | — | 0 | — |
| | 4 | — | 5 | — |
| | 1 | — | 0 | — |
| Abamectin | 1 | — | 2 | — |
| Hydramethylnon | 1 | — | 7 | — |
| Endosulfan | 16 | — | 13 | — |
| Bifenthrin | 63 | — | 1 | — |
| alpha-Cypermethrin | 63 | — | 0 | — |
| Flubendiamid | 63 | — | 0 | — |
| Indoxacarb | 16 | — | 0 | — |
| Ia + Acephate | 0.004 + 1 | 1:250 | 72 | 31 |
| Ia + Methamidophos | 0.004 + 1 | 1:250 | 78 | 35 |
| Bixafen + Deltamethrin | 0.004 + 11 | 1:250 | 29 | 0 |
| Bixafen + Abamectin | 0.004 + 1 | 1:250 | 28 | 2 |
| Bixafen + Hydramethylnon | 0.004 + 1 | 1:250 | 31 | 7 |
| Isopyrazam + Deltamethrin | 0.016 + 4 | 1:250 | 28 | 6 |
| Penflufen + Deltamethrin | 0.063 + 16 | 1:250 | 24 | 0 |
| Penflufen + Endosulfan | 0.063 + 16 | 1:250 | 34 | 13 |
| Sedaxane + Methamidophos | 0.25 + 63 | 1:250 | 48 | 20 |
| Sedaxane + Bifenthrin | 0.25 + 63 | 1:250 | 39 | 20 |
| Sedaxane + alpha-Cypermethrin | 0.25 + 63 | 1:250 | 48 | 20 |
| Sedaxane + Endosulfan | 0.063 + 16 | 1:250 | 34 | 13 |
| Sedaxane + Flubendiamid | 0.25 + 63 | 1:250 | 100 | 20 |
| Sedaxane + Indoxacarb | 0.063 + 16 | 1:250 | 21 | 0 |

USE EXAMPLE 5

Activity Against *Colletotrichum truncatum*

The stock solutions were mixed according to the ratio, pipetted onto a micro titer plate (MTP) and diluted with water to the stated concentrations. A spore suspension of *Colletotrichum truncatum* in an aqueous biomalt solution was then added. The plates were placed in a water vapor-saturated chamber at a temperature of 18° C. Using an absorption photometer, the MTPs were measured at 405 nm 7 days after the inoculation.

TABLE 13

| Active compounds/active compound mixture | Concentration [ppm] | Ratio | Observed efficacy | Calculated efficacy according to Colby (%) |
|---|---|---|---|---|
| Bixafen | 0.25 | — | 6 | — |
| Isopyrazam | 0.25 | — | 14 | — |
| Sedaxane (trans diastereoisomer) | 0.25 | — | 3 | — |
| Endosulfan | 63 | — | 8 | — |
| Flubendiamid | 63 | — | 0 | — |
| Bixafen + Endosulfan | 0.25 + 63 | 1:250 | 37 | 14 |
| Bixafen + Flubendiamid | 0.25 + 63 | 1:250 | 100 | 6 |
| Isopyrazam + Endosulfan | 0.25 + 63 | 1:250 | 43 | 21 |
| Sedaxane + Flubendiamid | 0.25 + 63 | 1:250 | 100 | 3 |

USE EXAMPLE 6

Activity Against *Leptospharium nodorum*

The stock solutions were mixed according to the ratio, pipetted onto a micro titer plate (MTP) and diluted with water to the stated concentrations. A spore suspension of *Leptosphaerium nodorum* in an aqueous biomalt solution was then added. The plates were placed in a water vapor-saturated chamber at a temperature of 18° C. Using an absorption photometer, the MTPs were measured at 405 nm 7 days after the inoculation.

TABLE 14

| Active compounds/ active compound mixture | Concentration [ppm] | Ratio | Observed efficacy | Calculated efficacy according to Colby (%) |
|---|---|---|---|---|
| Bixafen | 0.25 | — | 16 | — |
| Isopyrazam | 0.25 | — | 13 | — |
| Sedaxane (trans diastereoisomer) | 0.25 | — | 17 | — |
| Endosulfan | 63 | — | 5 | — |
| Chlorfenapyr | 63 | — | 8 | — |
| Flubendiamid | 63 | — | 22 | — |
| Bixafen + Endosulfan | 0.25 + 63 | 1:250 | 58 | 20 |
| Bixafen + Chlorfenapyr | 0.25 + 63 | 1:250 | 44 | 22 |
| Bixafen + Flubendiamid | 0.25 + 63 | 1:250 | 100 | 34 |
| Isopyrazam + Endosulfan | 0.25 + 63 | 1:250 | 68 | 18 |
| Sedaxane + Flubendiamid | 0.25 + 63 | 1:250 | 100 | 35 |

USE EXAMPLE 7

Activity Against *Fusarium culmorum*

The stock solutions were mixed according to the ratio, pipetted onto a micro titer plate (MTP) and diluted with water to the stated concentrations. A spore suspension of *Fusarium culmorum* in an aqueous biomalt solution was then added. The plates were placed in a water vapor-saturated chamber at a temperature of 18° C. Using an absorption photometer, the MTPs were measured at 405 nm 7 days after the inoculation.

TABLE 15

| Active compounds/ active compound mixture | Concentration [ppm] | Ratio | Observed efficacy | Calculated efficacy according to Colby (%) |
|---|---|---|---|---|
| Sedaxane (trans diastereoisomer) | 0.25 | — | 2 | — |
| Flubendiamid | 63 | — | 3 | — |
| Sedaxane + Flubendiamid | 0.25 + 63 | 1:250 | 100 | 5 |

B) Greenhouse Tests

The active substances were formulated separately or together as a stock solution comprising 25 mg of active substance which was made up to 10 ml using a mixture of acetone and/or dimethyl sulfoxide (DMSO) and the emulsifier Wettol EM 31 (wetting agent having emulsifying and dispersing action based on ethoxylated alkylphenols) in a volume ratio of solvent/emulsifier of 99 to 1. This solution was then made up to 100 ml using water. This stock solution was diluted with the solvent/emulsifier/water mixture described to the active substance concentration given below.

USE EXAMPLE 8

Activity Against Early Blight on Tomatoes Caused by *Phytophthora infestans* with Protective Application Young seedlings of tomato plants were grown in pots. The plants were sprayed to runoff with an aqueous suspension containing the concentration of active substance stated below. The next day, the treated plants were inoculated with an aqueous suspension of sporangia of *Phytophthora infestans*. After inoculation, the trial plants were immediately transferred to a humid chamber. After 6 days at 18 to 20° C. and a relative humidity close to 100%, the extent of fungal attack on the leaves was visually assessed as % diseased leaf area.

USE EXAMPLE 9

Curative Action Against *Puccinia recondita* on Wheat (Brown Rust of Wheat)

Leaves of potted wheat seedlings of the cultivar "Kanzler" were dusted with a suspension of spores of brown rust of wheat (*Puccinia recondita*). The plants were then placed in a chamber with high atmospheric humidity (90 to 95%), at 20-22° C., for 24 hours. During this time, the spores germinated and the germinal tubes penetrated into the leaf tissue. The next day, the infected plants were sprayed to runoff point with an aqueous suspension having the concentration of active substance stated below. After drying of the sprayed suspension, the test plants were returned into the greenhouse and cultivated at temperatures between 20 and 22° C. and at 65 to 70% relative atmospheric humidity for a further 7 days. The extent of the rust development on the leaves was then determined visually.

USE EXAMPLE 10

Protective Action against *Puccinia recondita* on Wheat (Brown Rust of Wheat)

Leaves of potted wheat seedlings of the cultivar "Kanzler" were sprayed to runoff point with an aqueous suspension having the concentration of active substance stated below. The next day, the treated plants were dusted with a suspension of spores of brown rust of wheat (*Puccinia recondita*). The plants were then placed in a chamber with high atmospheric humidity (90 to 95%), at 20-22° C., for 24 hours. During this time, the spores germinated and the germinal tubes penetrated into the leaf tissue. The next day, the test plants were returned into the greenhouse and cultivated at temperatures between 20 and 22° C. and at 65 to 70% relative atmospheric humidity for a further 7 days. The extent of the rust development on the leaves was then determined visually.

USE EXAMPLE 11

Protective Action Against *Blumeria graminis tritici* on Wheat (Mildew of Wheat)

Leaves of potted wheat seedlings of the cultivar "Kanzler" were sprayed to runoff point with an aqueous suspension having the concentration of active substance stated below. The next day, the treated plants were dusted with a suspension of spores of mildew of wheat (*Blumeria graminis tritici*). The plants were then returned into the greenhouse and cultivated at temperatures between 20 and 24° C. and at 60 to 90% relative atmospheric humidity for a further 7 days. The extent of the mildew development on the leaves was then determined visually.

USE EXAMPLE 12

Protective Action Against *Sphaerotheca fuliginea* on Cucumber (Mildew of Cucumber)

Leaves of potted cucumber seedlings (in the germ layer stage) were sprayed to runoff point with an aqueous suspension having the concentration of active substance stated below. The next day, the treated plants were dusted with a suspension of spores of mildew of cucumber (Sphaerotheca fuliginea). The plants were then returned into the greenhouse and cultivated at temperatures between 20 and 24° C. and at 60 to 80% relative atmospheric humidity for a further 7 days. The extent of the mildew development on the seed leaves was then determined visually.

The invention claimed is:

1. A mixture for controlling phytopathogenic harmful fungi selected from the group consisting of mixture (I), mixture (II) and mixture (III), wherein:
mixture (I) comprises as active ingredients
(1) at least one 1-methylpyrazol-4-ylcarboxanilide of the formula I

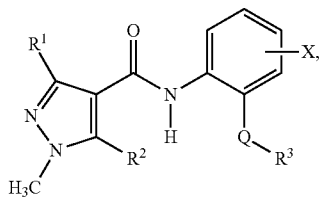

in which the substituents are as defined below:
$R^1$ is $C_1$-$C_4$-alkyl or $C_1$-$C_4$-haloalkyl;
$R^2$ is hydrogen or halogen;
X is hydrogen or fluorine;
Q is a direct bond;
$R^3$ is phenyl substituted with two or three halogen atoms, and
(2) a pyrethroid selected from the group consisting of allethrin, bifenthrin, cyfluthrin, cyhalothrin, cyphenothrin, cypermethrin, alpha-cypermethrin, beta-cypermethrin, zeta-cypermethrin, deltamethrin, fenpropathrin, lambda-cyhalothrin, permethrin, prallethrin, pyrethrin I, pyrethrin II, resmethrin, tefluthrin, tetramethrin, tralomethrin, profluthrin and dimefluthrin, in a synergistically effective amount;
mixture (II) comprises as active ingredients (1) penflufen and (2) deltamethrin in a synergistically effective amount; and
mixture (III) comprises as active ingredients (1) sedaxane and (2) a pyrethroid selected from the group consisting of deltamethrin, bifenthrin, cypermethrin, alpha-cypermethrin, beta-cypermethrin and zeta-cypermethrin, in a synergistically effective amount.

2. The fungicidal mixture of claim 1, wherein mixture (I) comprises a 1-methylpyrazol-4-ylcarboxanilide of the formula I where $R^1$ is $C_1$-$C_4$-haloalkyl, $R^2$ is hydrogen, Q is a direct bond and $R^3$ is phenyl substituted by two or three halogen atoms.

3. The fungicidal mixture of claim 1, comprising fluxapyroxad as the 1-methylpyrazol-4-ylcarboxanilide of the formula I.

4. The fungicidal mixture of claim 1, wherein the mixture is said mixture (II).

5. The fungicidal mixture of claim 1, further comprising an additional active compound in mixture (I), mixture (II) or mixture (III).

6. The fungicidal mixture of claim 1, comprising the components (1) and (2) in mixture (I), mixture (II) or mixture (III) in a weight ratio of from 100:1 to 1:100.

7. A composition, comprising at least one liquid or solid carrier and the mixture of claim 1.

8. A seed treated with the mixture of claim 1 in an amount of from 1 g to 1000 g per 100 kg of seed.

9. A seed treated with the mixture of claim 4 in an amount of from 1 g to 1000 g per 100 kg of seed.

10. A method for controlling phytopathogenic harmful fungi, comprising treating the fungi, their habitat or plants to be protected against fungal attack, the soil, seed, areas, materials or spaces with:
(I) (1) at least one compound of formula I

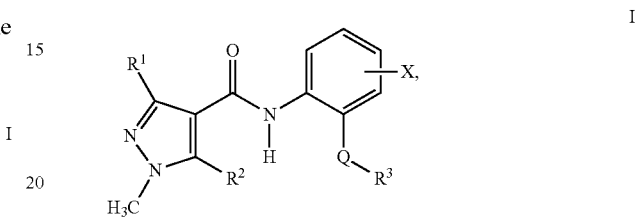

wherein
$R^1$ is $C_1$-$C_4$-alkyl or $C_1$-$C_4$-haloalkyl,
$R^2$ is hydrogen or halogen,
X is hydrogen or fluorine,
Q is a direct bond,
$R^3$ is phenyl substituted with two or three halogen atoms, and
(2) a pyrethroid selected from the group consisting of allethrin, bifenthrin, cyfluthrin, cyhalothrin, cyphenothrin, cypermethrin, alpha-cypermethrin, beta-cypermethrin, zeta-cypermethrin, deltamethrin, fenpropathrin, lambda-cyhalothrin, permethrin, prallethrin, pyrethrin I, pyrethrin II, resmethrin, tefluthrin, tetramethrin, tralomethrin, profluthrin and dimefluthrin, in a synergistically effective amount;
(II) (1) penflufen and (2) deltamethrin in a synergistically effective amount; or
(III) (1) sedaxane and (2) a pyrethroid selected from the group consisting of deltamethrin, bifenthrin, cypermethrin, alpha-cypermethrin, beta-cypermethrin and zeta-cypermethrin, in a synergistically effective amount.

11. The method according to claim 10, wherein the components (1) and (2) in (I), (II) or (III) are applied simultaneously as individual components or as a mixture, separately, or in succession.

12. The method according to claim 11, wherein the components (1) and (2) in (I), (II) or (III) are applied in an amount of from 5 g/ha to 2000 g/ha.

13. The method according to claim 11, wherein the components (1) and (2) in (I), (II) or (III) are applied in an amount of from 1 g to 1000 g per 100 kg of seed.

14. The method of claim 10, wherein component (1) in (I) is a 1-methylpyrazol-4-ylcarboxanilide of the formula I where $R^1$ is $C_1$-$C_4$-haloalkyl, $R^2$ is hydrogen, Q is a direct bond and $R^3$ is phenyl substituted by two or three halogen atoms.

15. The method of claim 10, wherein component (1) in (I) is fluxapyroxad.

16. The method according to claim 12, wherein component (1) in (I) is fluxapyroxad.

17. The method according to claim 13, wherein component (1) in (I) is fluxapyroxad.

* * * * *